United States Patent [19]

Carson et al.

[11] Patent Number: 4,689,986
[45] Date of Patent: Sep. 1, 1987

[54] VARIABLE FREQUENCY GAS-BUBBLE-MANIPULATING APPARATUS AND METHOD

[75] Inventors: Paul L. Carson, Ann Arbor, Mich.; Richard M. Detsch, Denver, Colo.

[73] Assignee: The University of Michigan, Ann Arbor, Mich.

[21] Appl. No.: 711,255

[22] Filed: Mar. 13, 1985

[51] Int. Cl.⁴ ............................................. G01N 29/02
[52] U.S. Cl. ........................................ 73/19; 73/61 R; 128/660
[58] Field of Search ................. 73/19, 61 R; 128/660, 128/663

[56] References Cited

U.S. PATENT DOCUMENTS

| | | | |
|---|---|---|---|
| 4,130,010 | 12/1978 | Wonn ........................................ | 73/19 |
| 4,442,843 | 4/1984 | Rasor et al. ............................ | 128/663 |
| 4,459,853 | 7/1984 | Miwa et al. ............................ | 128/660 |
| 4,483,345 | 11/1984 | Miwa ...................................... | 73/19 |

OTHER PUBLICATIONS

K. McCarty et al., "Frequency Modulated Ultrasonic Doppler Flow Meter", *Medical and Biological Eng.*, vol. 13, No. 1, pp. 59–64, Jan. 1975.

Primary Examiner—Stewart J. Levy
Assistant Examiner—Hezron E. Williams
Attorney, Agent, or Firm—Rohm & Monsanto

[57] ABSTRACT

A system for detecting gas bubbles in a specimen utilizes a transducer which produces pulses, illustratively of ultrasonic acoustic energy, having predetermined frequency characteristics. A first pulse has an increasing frequency with time, and a second pulse has a decreasing frequency with time. Imaging arrangements, which may be formed of ultrasonic transducers, produce images of the region within the specimen after exposure to each such pulse. In one embodiment, a growth transducer array is utilized for dramatically increasing the size of the bubbles, which array is formed of a plurality of transducers which are moved with respect to the specimen and which have respective frequency characteristics over different frequency ranges. Thus, bubble radius is successively increased as each bubble is exposed to the acoustic energy from each such transducer within the growth transducer array. The present invention can be used to reduce the cavitation threshold of bubbles, particularly in the vicinity of tumors, or to increase the temperature in the bubble-containing region.

32 Claims, 6 Drawing Figures

VARIABLE FREQUENCY GAS-BUBBLE-MANIPULATING APPARATUS AND METHOD

BACKGROUND OF THE INVENTION

This invention relates generally to gas bubble detector systems and tissue therapeutic systems which utilize ultrasonic acoustic and/or electromagnetic energy, and more particularly, to a system which controls the dimensions of gas bubbles and selectably transient cavitation phenomena by controlling the energy fields as a function of frequency, time, and pulse repetition rate.

It is known that acoustic or electromagnetic energy which is propagated through a medium, such as a liquid, is scattered by the presence of gas bubbles. Such scattering permits detection of bubbles within the medium. The amount of the energy which is scattered is a function of the size, or radius, of the individual bubbles. Generally, at the resonant ultrasonic frequency, or at a lower frequency, the detection process is improved if the size of the bubbles is increased. Such an increase in the size of the bubbles may render detectable bubbles which were previously too small to be detected.

Bubble oscillation and resultant growth of the bubble, as well as scattering of energy from the bubble; is maximum for a limited frequency range when the frequency is at the resonant frequency for a given bubble size, and other conditions are met. Alternatively, the scattering of energy at a given frequency is maximized when the bubbles are at the resonant size. Bubble can be caused to grow in size by the process of rectified diffusion during acoustically-induced oscillations. Within a narrow distribution of bubble sizes, the maximum bubble oscillation amplitude and therefore scattering and rate of growth should be realized when the frequency of the ultrasonic acoustic energy starts at the resonant frequency for the bubbles and decreases slowly as the bubbles grow and their resonant frequency decreases. With a wide distribution of bubble sizes, a large amount of scattering and bubble growth will still result when the frequency starts high and is swept lower to reach the resonant frequency and begin rapid growth of an increasing number of the available bubbles.

In one known system for monitoring the rate of flow of blood and the blood pressure, gaseous bubbles are introduced into the blood stream and then subjected to ultrasonic energy. The scattered energy is detected at first and second points having a predetermined distance therebetween, thereby permitting a determination of blood velocity. Additionally, monitoring of the size of a bubble provides an indication of blood pressure since the size of a bubble is related to the pressure. Although this known system monitors gas bubbles at various locations quantitatively to determine bubble size changes, this system cannot provide an indication of the size of bubbles already present in the blood stream, such as those which accompany decompression sickness, or the bends. Instead, the known system monitors the size of a bubble which is injected into the blood stream.

The conventional technique for determining the presence of bubbles in the blood stream utilizes a Doppler shift in the frequency of the ultrasonic acoustic energy which is reflected by the blood. It is now well known that the amplitude of the Doppler bubble signal increases nearly proportionally with increases in the radius of the bubble. It is a problem with Doppler systems that notwithstanding the electronic signal processing systems presently available, the human hearing mechanism represents the most acurate processor for recognizing whether bubble signals are present or absent. This results from the fact the human hearing mechanism can recognize the sinusoidal narrow-band "chirping" quality signals at amplitudes which are lower than the spectral signal of the Doppler blood flow. Thus, a skilled human operator is required if satisfactory results using Doppler blood flow monitoring equipment are to be achieved.

Accordingly, it is an object of the invention to provide a gas bubble detector which is relatively inexpensive and easy to use.

It is also an object of this invention to provide a gas bubble detector having increased sensitivity over known detector systems.

It is another object of this invention to provide a system for detecting gas bubbles in a fluid, the system being capable of detecting previously undetectably small bubbles.

It is another object of this invention to provide a bubble manipulation apparatus which can cause bubbles to be varied in size.

It is additionally an object of this invention to provide a bubble detection system which produce multidimensional images.

It is a further object of this invention to provide a method for detecting bubbles wherein energy in the form of sound is utilized to alter the detectability of bubble-containing regions within a fluid.

It is yet another object of this invention to provide a system for detecting bubbles within tissues.

It is a still further object of this invention to provide an imaging arrangement wherein a plurality of images are combined mathematically to produce a final image of a bubble-containing region.

It is still another object of this invention to provide a system wherein transducer required during examination of a patient is minimized.

An additional object of the present invention is to provide an imaging system which utilizes electromagnetic energy pulses to effect detectability of gas bubbles in a fluid.

Another object of this invention is to provide a therapeutic system for selectably adjusting a cavitation threshold in a bubble-containing region.

A still further object of this invention is to provide a therapeutic system which utilizes electromagnetic energy and/or ultrasonic acoustic energy to control a temperature in a predetermined region within a fluid or a tissue.

A yet additional object of this invention is to provide an imaging system which is provided with feedback for monitoring bubbles being altered in size to determine an optimal pulse wave form for energizing the bubbles.

A yet further object of this invention is to provide a system which uses electromagnetic or acoustic energy to effect changes in the size of bubbles within a fluid or a tissue, and then utilize electromagnetic energy to effect bubble detection.

SUMMARY OF THE INVENTION

The foregoing and other objects are achieved by this invention which provides a gas bubble detection system which utilizes a variable frequency spectrum which permits control over the size of the bubbles within a liquid. In one embodiment of the invention which utilizes ultrasonic acoustic energy, at least one ultrasonic transducer is provide for emitting acoustical energy at variable frequencies so as to permit changes in the radius of each bubble. A detecting transducer, which may be the emitting transducer, receives at least a portion of the ultrasonic acoustic energy which has been scattered by the bubbles.

As is known, acoustic and electromagnetic waves are scattered by gas bubbles, thereby allowing regions within a fluid under examination which contains bubbles to be detected. The amount of energy which is scattered increases substantially with increases in bubble radius, except at a short range of radii above the resonant radius. Therefore, regions within the fluid which contain bubbles will cause more scattering if the bubbles are caused to be enlarged. Such enlargement of the bubbles causes an increasre in the sensitivity of the bubble detection arrangements. The sensitivity can be increased further if the object is examined twice, once before and once after the bubbles are caused to increase in size. The results of the two examinations are combined subtractively, or by other processing, such as weighted, normalized difference, to highlight the regions which contain bubbles. Thus, the bubbles become a contrast-providing agent.

The present invention does not depend upon the source of the bubbles. Accordingly, the apparatus and method of the present invention will be useful in detecting regions within a tissue or fluid, such as the blood stream, which probably contains a small number of gas bubbles naturally, as well as for regions which have had bubbles introduced as a contrast agent. Thus, medical scanners can use the present variable frequency system of achieving bubble growth to change the size of the bubbles already present in the blood stream, or tissues with or without gas-producing pathology, or of bubbles which are injected into the blood stream.

Similar bubble manipulating and detection techniques can be used for numerous industrial applications. Thus, bubble growth and monitoring of the scattering might make it possible to detect and quantify size or amount of bubbles in pipelines where the bubbles are too small or too few for detection by known arrangements and methods. Bubble growth may also be employed to reduce friction in pipelines and on the surfaces of ships and submarines. Also, extraction of gas from the water around the ships and submarines would allow a limited supply of gas to last longer. Microscopic bubbles might be incorporated into a friction-reducing slime and the bubbles increased in size to improve the effectiveness of the slime on demand by sonification. This might be achieved by providing a coating on the vessel which is relatively hard when the vessel is stationary, or moving slowly. However, the coating could be made softer and slicker by the application of ultrasonic or electromagnetic energy, or by some other activation such as resonant bubble heating. Small gas bubbles cannot pass through the blood vessels in the lungs. However, such passage can be achieved by encapsulated gas bubbles having diameters of less than five microns. When the encapsulation dissolves or otherwise allows rectified diffusion, such gas bubbles are then detectable in accordance with the principles of the present invention at concentrations and/or sizes which are lower than those required for imaging using conventional ultrasonic equipment. Passage of the bubbles through the lungs is important since this would allow imaging of most parts of the body with an intravenous injection which is considerably less dangerous than an arterial injection.

In accordance with a highly advantageous embodiment of the invention, an arrangement is provided which generates an ultrasonic acoustic energy or electromagnetic energy field of vary frequency and/or repetition rate such that the growth of bubbles is enhanced. Additionally, other devices are provided which produce an image of all or part of the regions containing bubbles. In one embodiment, an ultrasonic acoustic, single-array bubble detection device is provided with two transducer elements arranged in annular relationship with one another. One element is used for sending pulses of ultrasonic acoustic energy of changing frequency, and the other element detects the returning echo signals caused by scattering and reflection with in the specimen being tested. The sending transducer in this embodiment, emits two types of ultrasonic energy pulses; the frequencies of which vary with time. A first type of pulse has an ultrasonic frequency which varies upwardly with time, while a second type of pulse has a frequency which varies downwardly with time. Since the optimal frequency for growing bubbles decreases with increases in radius, a pulse of the second type is used to induce bubble growth.

In accordance with a method aspect of the invention, a procedure is provided for detecting the depths, along the transducer array's acoustical axis, at which bubbles are contained within the specimen. First, a pulse, or series of pulses, of the first type is emitted at a given location, and since this first type pulse has an increases frequency with time, minimal bubble growth is produced. Subsequently, a pulse, or series of pulses, of a second type, having a decreasing frequency with time, is emitted at the same location as the first type pulse. Preferably, the variations in the frequency of the second type of pulse correspond to the variations in the frequency of the type of pulse. The reflected signals are compared for each type of pulse; the comparison being produced using filters which are matched to the transmitting wave forms. The regions where the two received echo signals differ from ane another correspond to regions which contain bubbles. An image of the region or object containing the bubbles can be constructed by combining information obtained from repeated applications of this procedure at various array locations. Additionally, predetermined characteristics of the bubbles, their contents, and their region can be learned from determining the rate at which the bubbles increase in size.

In accordance with an embodiment of the invention, two transducer arrays are provided for obtaining respective images of the regions interior of the specimen. Additionally, a growth transducer array is provided to cause bubble growth. The entire array system, including the first and second transducer arrays, and the growth array interposed therebetween, is passed over the specimen at a constant velocity which allows for the production of two separate images resulting from the ultrasonic acoustic energy signals sent by the first and second transducer arrays, respectively. However, during the scanning process, the growth transducer array is causing the bubbles between the fields of the first and second arrays to grow. Thus, the first and second images differ from one another in those areas where bubbles are contained.

In one embodiment of the invention, the growth transducer array is formed of a plurality of transducers which simultaneously produce wave trains of acoustical energy of equal duration. However, each transducer within the growth array produces a different range of frequencies. As the separate transducers in the growth transducer array pass over a given gas bubble, the bubble experiences sound of decreasing frequency causing the bubble radius to increase with time. Preferably, the bubble radius is increased rapidly, and the length of each pulse from each of the four transducers is such that the stationary bubbles in the sound field of each transducer experience at least one complete pulse from the transducer before being exposed to the field of the next transducer.

The frequency-shift system of the present invention can be used to detect the velocity of bubbles in regions where bubbles may be moving, such as in bubble-containing blood which passes through a blood vessel. The amount of bubble growth depends upon the relative velocity between the transducer array and the bubbles; the velocity of the bubbles being parallel to the direction of transducer movement. The velocity can be determined with greater precision by considering bubble growth for two different transducer paths. If the relative velocity is large, the bubbles will only be in the field of the growth transducer array for a short period of time, resulting in little bubble growth. Thus, there will not be a large difference between the first and second images. However, if the relative velocity is small, the bubbles will be in the growth field for a longer period of time resulting in more bubble growth, and therefore a larger contrast between the first and second images. By imaging along several planes, it is possible to evaluate the velocity of the bubbles quantitatively.

In accordance with a further and significant aspect of the invention, the system and method of the present invention can be utilized therapeutically to damage preferentially certain types of tumors or infections. It is known that transient cavitation occurs when sound-induced oscillations in bubble radius are large enough to cause bubble collapse. Transient cavitation is a violent phenomenon which can readily cause biological damage. The threshold intensity for transient cavitation decreases with increasing bubble radius, for bubbles smaller than approximately two hundred microns. Thus, when it is desirable to cause biological damage to bubble-containing regions without causing damage to other regions, the frequency-shift method of the present invention can be used to lower the acoustic intensity for tissue damge. It is therefore possible to damage preferentially certain types of tumors or infections which have an existing or induced high bubble content. In this case, the frequency-shift method can be used to increase the radius of the bubbles within the tumor, verify the acoustic beam location, and make it possible to cause cavitation in the tumor using relatively low ultrasonic acoustic energy levels. Thus, the healthy tissue would not be subjected to potentially dangerous, high intensity ultrasonic radiation.

In accordance with a further aspect and feature of the invention, the present frequency-shift system may serve as an ultrasenstive, in vivo, method for determining the presence or absence of small bubbles within the body. Small bubbles occur normally in very low concentrations in some parts of the human body, such as the blood. However, the concentration or adsence of bubbles has not been determined for most tissue other than those having certain bubble-producing pathologies. The absence of such information pertaining to the presence or absence of bubbles hinders evaluation of the propriety or safety of using clinical ultrasonic acoustic energy system. The present frequency-shift system can be used to increase bubble radius, thereby providing a means of detecting bubbles which are too small to be detected safely with constant-frequency devices. Additionally, the final radius of enlarged bubbles would be quantitatively related to the initial bubble size. Thus, the frequency-shift method permits a determination of which tissues contained bubbles, and also the size of such bubbles.

BRIEF DESCRIPTION OF THE DRAWINGS

Comprehension of the invention is facilitated by reading the following detailed description in conjunction with the annexed drawings, in which.

DETAILED DESCRIPTION

Figure 1:
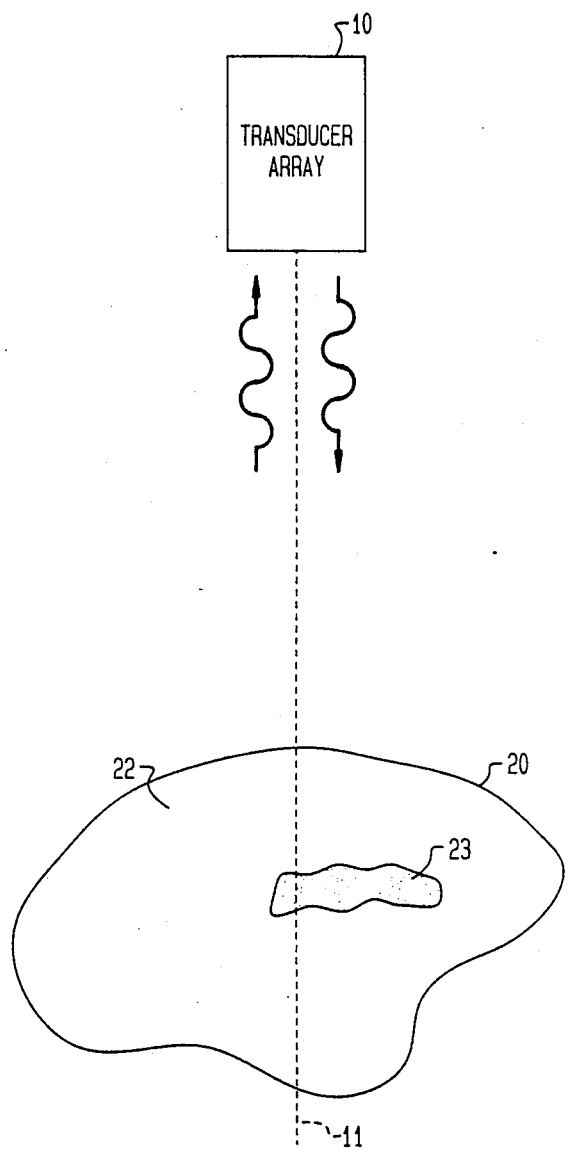
FIG. 1 is a schematic representation of a transducer array communicating ultrasonically with a specimen containing a bubble region.

FIG. 1 shows a transducer array emitting ultrasonic acoustic energy substantially along an array axis 11 into a specimen 20. As shown in the figure, specimen 20 defines a volume 22 which is shown to have a bubble region 23. Ultrasonic acoustic energy which is reflected from specimen 20 and the bubbles in bubble region 23 is returned to transducer array 10, substantially along array axis 11.

Figure 2:
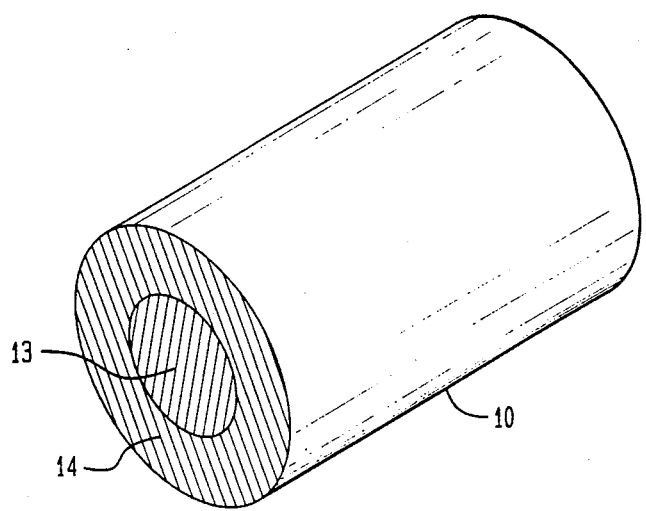
FIG. 2 is a schematic representation of an annular ultrasonic transducer array.

FIG. 2 is a schematic representation of transducer array 10 having two transducer elements, 13 and 14, arranged in an annular fashion. In this embodiment, one of the transducer elements is used to emit pulses of changing frequency, while the other transducer element detects the returning signals, or echos, caused by scattering and reflections within the specimen.

In accordance with the invention, the emitting transducer element of transducer array 10 is adapted to send ultrasonic acoustic pulses of changing frequency. Essentially, there are emitted first and second types of ultrasonic acoustic pulses; the first type of ultrasonic acoustic pulse being characterized by an increasing frequency characteristic with respect to time, while the second type of ultrasonic acoustic pulse has a frequency characteristic which decreases with time. An ultrasonic energy pulse of the second type is used to produce an enlargement in the size of the bubbles contained with the specimen. Thus, the present invention contemplates within its scope a method for detecting with great sensitivity the particular depth along the array axis where bubbles are contained within the specimen. First, an ultrasonic energy pulse of the first type having an increasing frequency characteristic is emitted into the specimen. The increasing frequency causes minimal bubble growth. Subsequently, and ultrasonic acoustic energy pulse of the second type, having a decreasing frequency characteristic is emitted into the specimen from the transducer array. Preferrably, the first and second types of ultrasonic acoustic energy pulses vary over equal frequency ranges, but reversed in time. Filters (not shown) which are matched to the transmitting wave forms are used to compare the reflected signals from both ultrasonic acoustic energy pulses. The regions within the specimen where the two received ultrasonic acoustic energy pulses differ from one another correspond to the depths where the bubbles are located. Using this technique, an image of the object can be constructed by combining information obtained from repeated use of the precedure at various array locations.

Figure 3A:
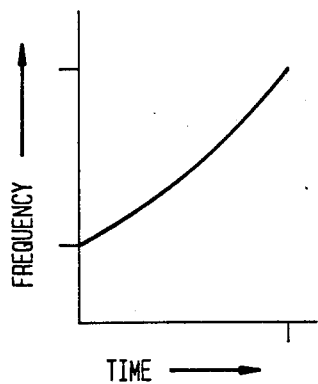
FIG. 3A and 3B are graphical representations of ultrasonic acoustic frequency characteristics which vary positively and negatively, respectively, in time.
Figure 3B:
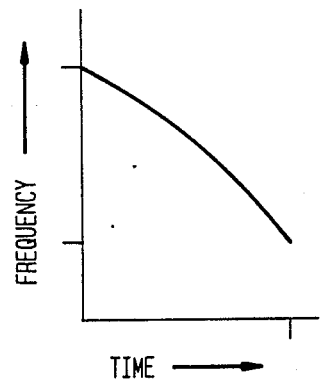

FIGS. 3A and 3B show the frequency characteristics of the first and second types of ultrasonic acoustic energy pulses. FIG. 3A shows the frequency of the energy pulse to be increasing with respect to time. FIG. 3B, on the other hand, shows that the frequency of the second type of ultrasonic acoustic energy pulse decreases with time. In this particular embodiment, the frequency range over which the ultrasonic acoustic energy pulses vary is the same for each type of pulse.

Figure 4:
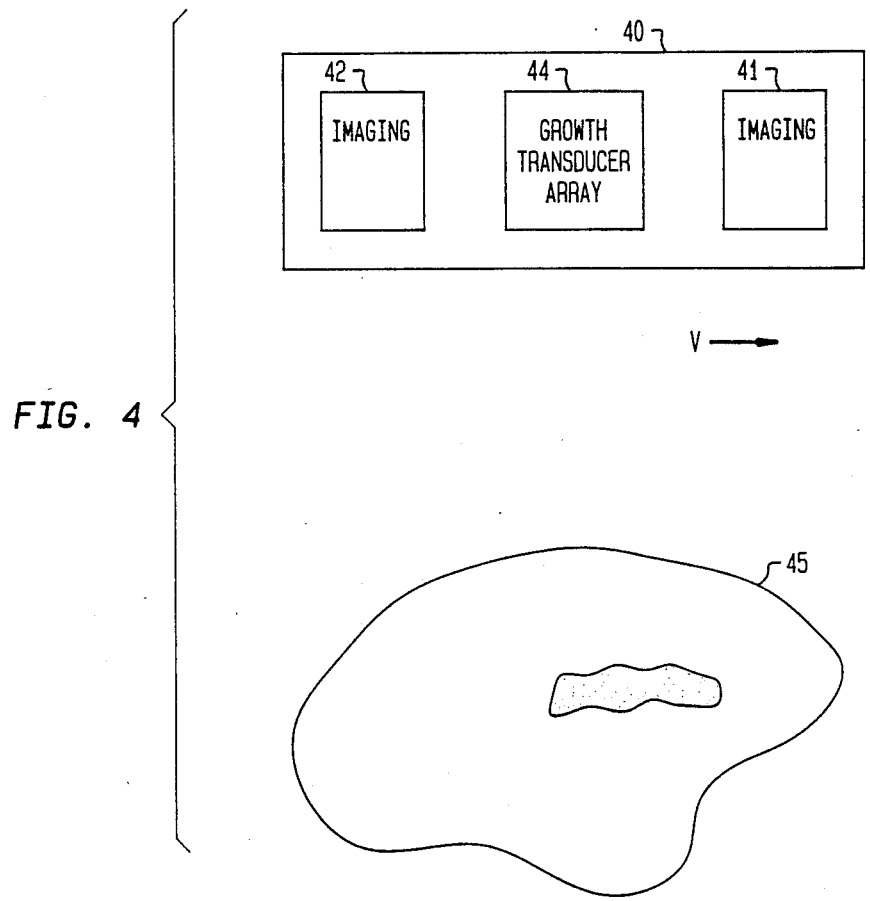
FIG. 4 is a schematic representation of a transducer array having a pair of imaging transducers with a growth transducer array arranged there between moving with respect to a specimen.

FIG. 4 shows an acoustic transducer array 40 which is paricularly useful in the frequency-shift system of the present invention for imaging objects containing gas bubbles. Ultrasonic acoustic transducer array 40 is provided with first and second imaging transducer arrays, 41 and 42 respectively, each for producing an image of a specimen 45. A growth transducer array 44 is arranged on ultrasonic acoustic transducer array 40 intermediate of imaging transducer arrays 41 and 42. Growth transducer array 44 is used to cause bubble growth. In this embodiment, the entire ultrasonic acoustic transducer array 40 is passed over specimen 45 at a constant velocity V which is slow enough to permit construction of two separate images from imaging transducer arrays 41 and 42. During the scanning process, growth transducer array 44 is causing the bubbles between the fields of ultrasonic acoustic energy from the imaging transducer arrays to grow. Thus, the images produced by the imaging transducer arrays differ in those areas where bubbles are contained.

Figure 5:
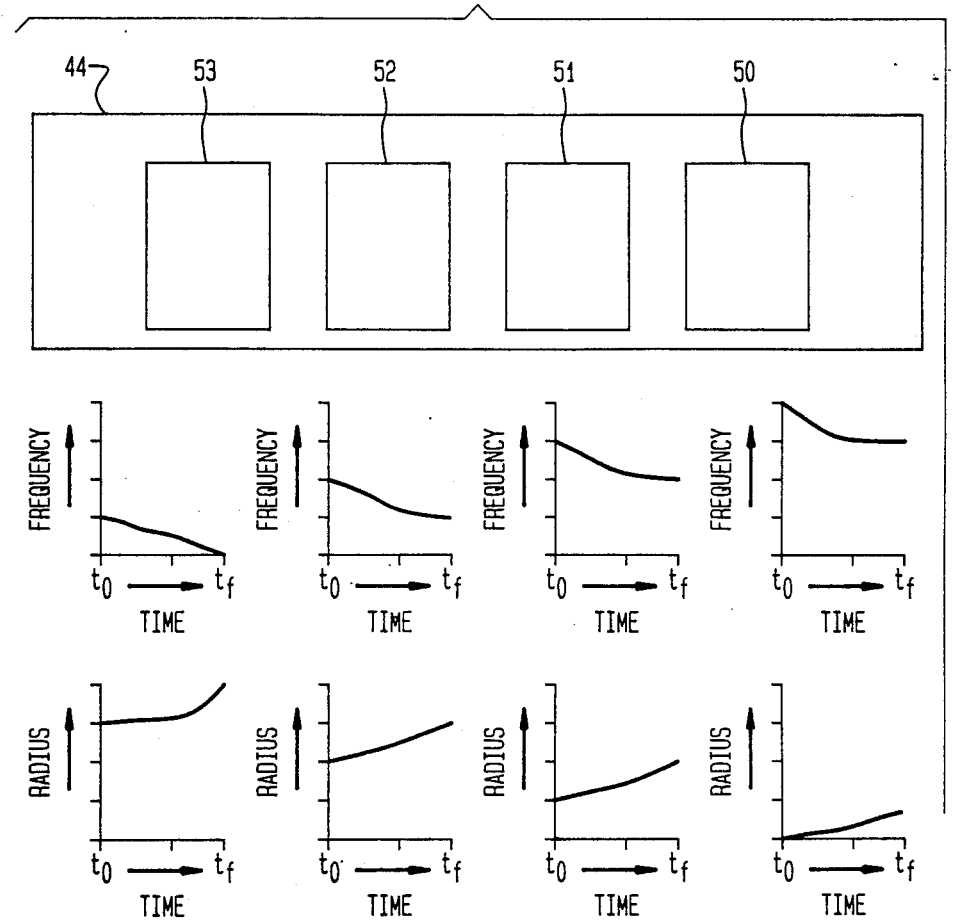
FIG. 5 is a schematic and graphical representation of a growth transducer array, each transducer in the array having a specific frequency characteristic.

FIG. 5 is a schematic representation of growth transducer array 44. As shown in this figure growth transducer array 44 is provided with four growth transducers 50 to 53. Also, in FIG. 5, a plot of transducer frequencies as a function of time is arranged beneath each of the growth transducers. As the array is passed over a given bubble, the bubble experiences ultrasonic acoustic energy of decreasing frequency, thereby causing the bubble radius to increase rapidly. The duration of the pulses ($t_f$-$t_o$) is such that a stationary bubble in the sound field of one transducer experiences at least one complete pulse from each growth transducer. For example, a stationary bubble will experience a complete pulse from growth transducer 50 before it is subjected to the pulse from growth transducer 51. FIG. 5 further shows a plot of bubble radius as a function of time. As is evident from the drawing, decreases in the frequency of each pulse will cause a corresponding increase in the radius of a given bubble.

The frequency-shift method of the present invention can also be used to detect the velocity of bubbles in regions where bubbles may be moving, such as in bubble-containing blood passing through a vein. As discussed hereinabove, with respect to FIG. 4, growth transducer array 44 passes over the bubbles over specimen 45 with a velocity V. The amount of bubble growth depends upon the relative velocity between the growth transducer array and the bubbles, V-$V_B$, where $V_B$ is the velocity of the bubble in the direction of the motion of the growth transducer array. If the relative velocity between the bubbles and the growth transducer array is large, the bubbles will only be in the growth field for a short period of time, thereby resulting in only small amount of bubble growth. In such a situation, only a limited difference will exist between the image produced by imaging transducer arrays 41 and 42. However, if the relative velocity is small, the bubbles will be in the field of the growth transducer array for a relatively long period of time, resulting a greater bubble growth and higher difference between the images of the imaging transducer arrays. By imaging along several planes, it is possible to evaluate the actual bubble velocity.

As noted hereinabove, the present invention be utilized to damage preferentially tumors and infections which have either an existing or an induced high bubble content. The present frequency-shift system can be used to increase the dimensions of the bubbles within the tumor such that its location can be verified and transient cavitation can be caused to occur within the tumor at relatively low acoustic intensities. The use of such low intensity would prevent damage to healthy tissue.

Although the invention has been described in terms of specific embodiments and applications, persons skilled in the art, in light of this teaching, can generate additional embodiments without exceeding the scope or departing from the spirit of the claimed invention. Accordingly, it is to be understood that the drawings and descriptions in this disclosure are proffered to facilitate comprehension of the invention and should not be construed to limit the scope thereof.

What is claimed is:

1. A bubble detection method of the type which utilizes ultrasonic acoustical energy to detect a bubble-containing region within a specimen, the bubble detection method comprising the steps of:
    emitting from an ultrasonic transducer the acoustical energy into the bubble-containing region within the specimen;
    decreasing the frequency of the acoustical energy with respect to time whereby the size of a bubble in the bubble-containing region is increased; and
    receiving a portion of said emitted acoustical energy reflected by said bubble of increased size within the bubble-containing region.

2. The bubble detection method of claim 1 comprising the further step of moving an acoustical energy wave pattern produced by said ultrasonic transducer with respect to the specimen for producing a multidimensional image.

3. The bubble detection of claim 1 wherein said step of receiving comprises the step of receiving with a receiving transducer said portion of said acoustical energy emitted from said ultrasonic transducer.

4. The bubble detection method of claim 1 wherein there is provided the further step of producing a first image of the specimen.

5. The bubble detection method of claim 4 wherein there is further provided the step of producing a second image of the specimen after performing said step of decreasing.

6. The bubble detection method of claim 5 wherein there is provided the further step of comparing said first and second images for determining a selected characteristic property of the bubble-containing region.

7. The bubble detection method of claim 1 wherein there is provided the further step of further emitting from a further ultrasonic transducer acoustical energy having, with respect to time, a further decreasing frequency into the specimen for responsively further increasing the size of said bubble in the bubble-containing region.

8. The bubble detection method of claim 7 wherein said steps of emitting and further emitting occur during respective, sequential time periods.

9. The bubble detection method of claim 8 wherein said sequential time periods have equal durations.

10. The bubble detection method of claim 1 wherein prior to said step of emitting there is provided the further step of prior emitting acoustical energy having a frequency which increases with time into the specimen for responsively decreasing the size of a bubble in the bubble-containing region.

11. The bubble detection method of claim 10 wherein said decreases and increases in said frequencies with respect to time during said steps of emitting and prior emitting, respectively, occur within equal upper and equal lower frequencies.

12. The bubble detection method of claim 11 wherein said decreases and increases in said frequencies occur during time periods having equal durations whereby said decreases and increases in said frequencies are time-reversed with respect to one another.

13. The bubble detection method of claim 10 wherein said ultrasonic transducer is formed as a transducer array having a first transducer surrounding a second transducer.

14. The bubble detection method of claim 1 wherein there is provided the further step of reducing a transient cavitation threshold for causing collapse of the bubbles in the bubble-containing region.

15. The bubble detection method of claim 14 wherein said decrease in said frequency is sufficient to cause a catastrophic collapse of the bubbles in the bubble-containing region.

16. The bubble detection method of claim 15 wherein said amplitude of said acoustical energy is insufficient to damage healthy tissue outside of the bubble-containing region.

17. The bubble detection method of claim 1 wherein said size of said bubble is increased from a size which is undetectable to a detectable size.

18. An imaging arangement of the type which utilizes emitted energy to detect gas bubbles within a region of a specimen, the arrangement comprising:
growth array means formed of a plurality of transducers substantially aligned along an axis, each for emitting a respective energy having a frequency which decreases with time over a respective frequency range, whereby the gas bubbles within the specimen are enlarged;
translation means for displacing said growth array means with respect to the specimen in a direction substantially along said axis; and
imaging means for producing a first image of the region of the specimen prior to the region being exposed to said emitted energy, and a second image of the region responsive to exposure of the region to said emitted energy.

19. The imaging arangement of claim 18 further comprising comparison means for comparing said first and second images to determine the presence of the gas bubbles in the region of the specimen.

20. The imaging arrangement of claim 19 wherein said comparison means comprises:
matched first and second filters for detecting echo signals reflected from within the specimen; and
subtraction means for producing a third image showing said presence of the gas bubbles in said region of the specimen by a selectable one of mathematical subtraction and normalized, weighted subtraction techniques.

21. The imaging arrangement of claim 19 wherein there is further provided measurement means for quantitatively measuring the amount of bubble enlargement in response to said growth array means.

22. The imaging arrangement of claim 21 wherein there is further provided means for determining bubble velocity.

23. The imaging arrangment of claim 21 wherein there is further provided means for determining an original bubble size.

24. The imaging arrangement of claim 21 wherein there is further provided means for determining a numerical density of bubbles.

25. The imaging arrangement of claim 21 wherein said growth array means comprises a phased acoustic transducer array for reducing the need for displacing said growth array means.

26. The imaging arrangement of claim 25 wherein said phased acoustic transducer array is characterized by a varying frequency.

27. The imaging arrangement of claim 18 wherein said growth array means is arranged to emit a plurality of electromagnetic pulses for absorption within the gas bubbles whereby a radius of each bubble is increased during each of said electromagnetic pulses.

28. The imaging arrangement of claim 18 wherein said growth array means is arranged to emit ultrasonic acoustic energy.

29. The imaging arrangement of claim 18 used for reducing a transient cavitation threshold in the gas bubbles.

30. The imaging arrangement of claim 18 used for increasing a temperature in the vicinity of the gas bubbles.

31. An imaging arrangement for producing a visible indication responsive to gas bubbles contained within a region of a specimen, the imaging arrangement comprising:
pulse means for producing a first pulse of acoustical energy having a frequency which increases with time, said first pulse being directed into the region of the specimen, and a second pulse of acoustical energy having a frequency which decreases with time, said second pulse also being directed into the region of the specimen and causing the gas bubbles contained within the region of the specimen to increase in size; and
imaging means for forming a first image of the region after being exposed to said first pulse, and a second image of the region after being exposed to said second pulse.

32. The imaging arrangement of claim 31 wherein there is further provided feedback means responsive to said imaging means for determining an optimal frequency for optimizing a difference between said first and second images.

* * * * *